United States Patent [19]

Williams et al.

[11] Patent Number: 5,215,523
[45] Date of Patent: Jun. 1, 1993

[54] BALLOON CATHETER INFLATION SYRINGE WITH REMOTE DISPLAY

[75] Inventors: Eli Williams, 700 W. 200 North, North Salt Lake, Utah 84054; Evan Call, Bountiful; Arlee Swensen, Layton, both of Utah

[73] Assignee: Eli Williams, North Salt Lake, Utah

[21] Appl. No.: 791,475

[22] Filed: Nov. 12, 1991

Related U.S. Application Data

[63] Continuation-in-part of Ser. No. 707,671, May 30, 1991, abandoned.

[51] Int. Cl.⁵ .................. A61M 29/00; A61M 1/00
[52] U.S. Cl. ................................ 604/97; 604/121
[58] Field of Search ............ 128/903, 904, 709-712, 128/633; 604/96, 97, 98, 65-67, 118, 121

[56] References Cited

U.S. PATENT DOCUMENTS

| | | | |
|---|---|---|---|
| 4,447,224 | 5/1984 | DeCant, Jr. et al. | 604/67 |
| 4,677,982 | 7/1987 | Llinas et al. | 128/664 |
| 4,714,462 | 12/1987 | DiDomenico | 604/67 |
| 4,723,554 | 2/1988 | Oman et al. | 128/664 |
| 4,759,369 | 7/1988 | Taylor | 128/633 |
| 4,846,191 | 7/1989 | Brockway et al. | 128/748 |
| 4,940,459 | 7/1990 | Noce | 604/98 |
| 4,952,928 | 8/1990 | Carroll et al. | 340/825.54 |
| 4,974,607 | 12/1990 | Miwa | 128/904 |
| 4,985,015 | 1/1991 | Obermann et al. | 604/67 |
| 5,021,046 | 6/1991 | Wallace | 604/97 |
| 5,084,060 | 1/1992 | Freund et al. | 606/192 |

*Primary Examiner*—John D. Yasko
*Assistant Examiner*—Adam J. Cermak
*Attorney, Agent, or Firm*—Trask, Britt & Rossa

[57] ABSTRACT

Apparatus for remotely displaying the inflation pressure within an inflator for inflating a balloon catheter. The apparatus comprises a pressure transducer positioned to sense pressure within the syringe, a transmission unit receiving a pressure signal from the transducer and transmitting by means of infrared light pulse sequences, a pressure message reflective of the pressure signal. A monitor positionable at a distance from the transmission unit receives and decodes the pressure messages, and provides a display thereof. A timer key for initiating the transmission of start/stop clock messages is located on the inflator unit. The monitor further includes a timer responsive to received clock messages, and an elapsed time display.

27 Claims, 7 Drawing Sheets

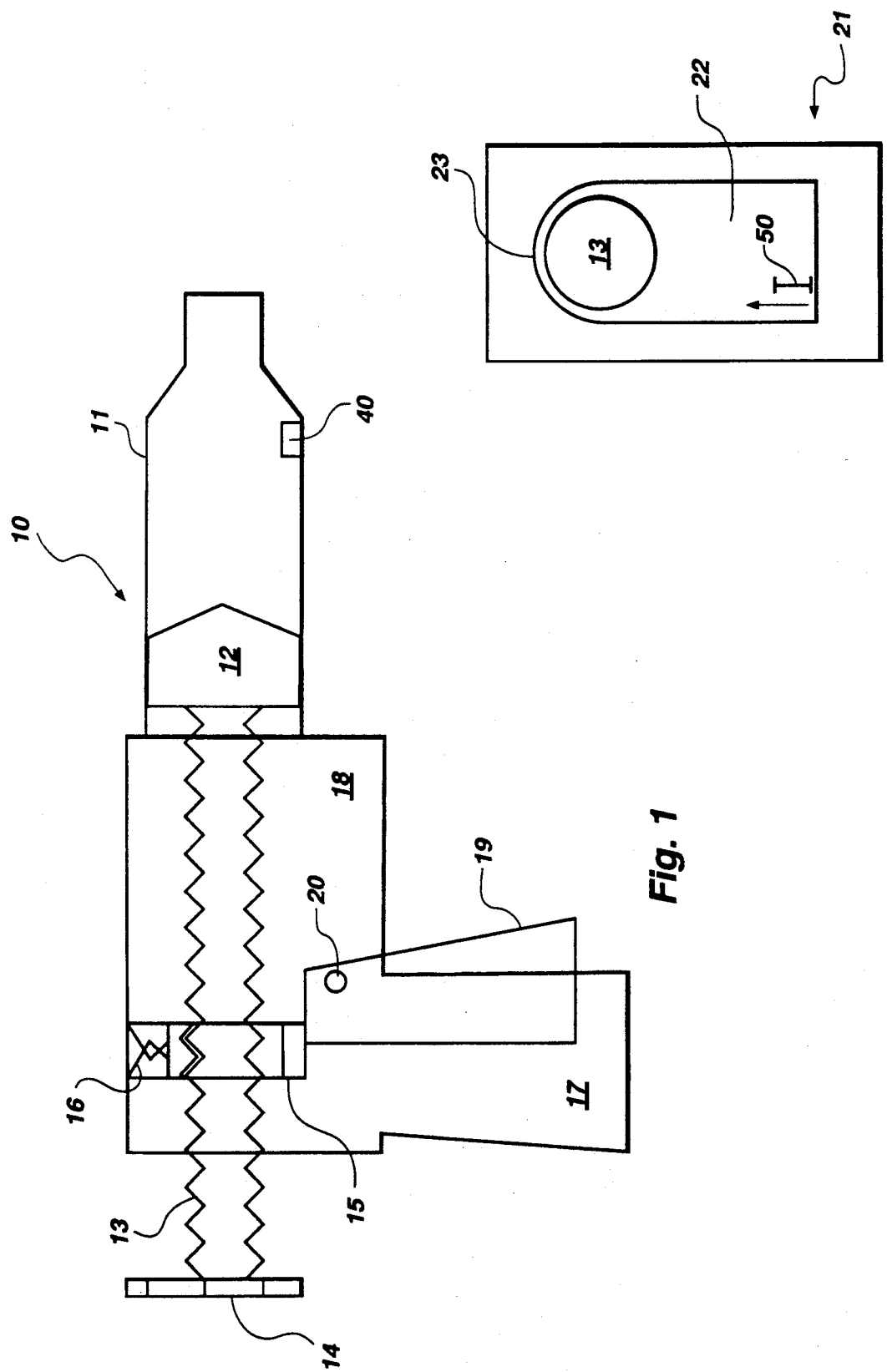

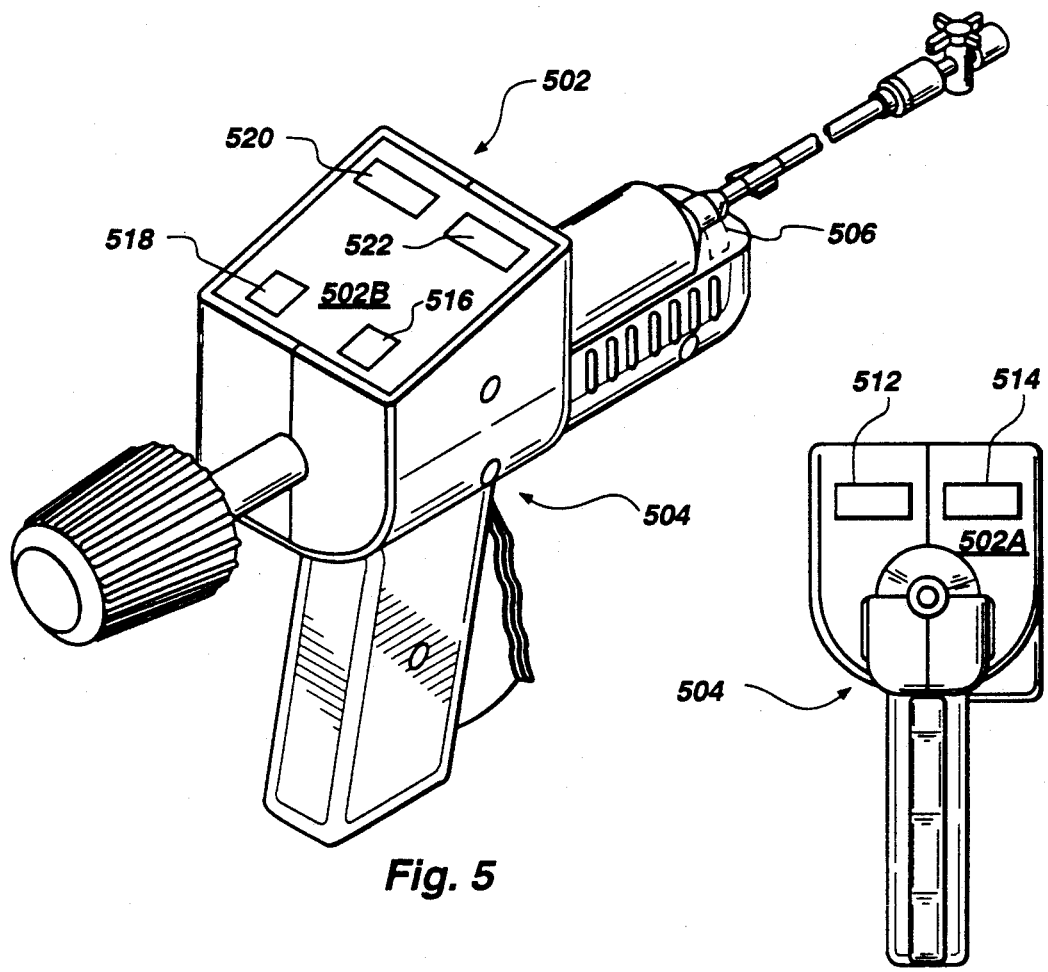
Fig. 5
Fig. 5A
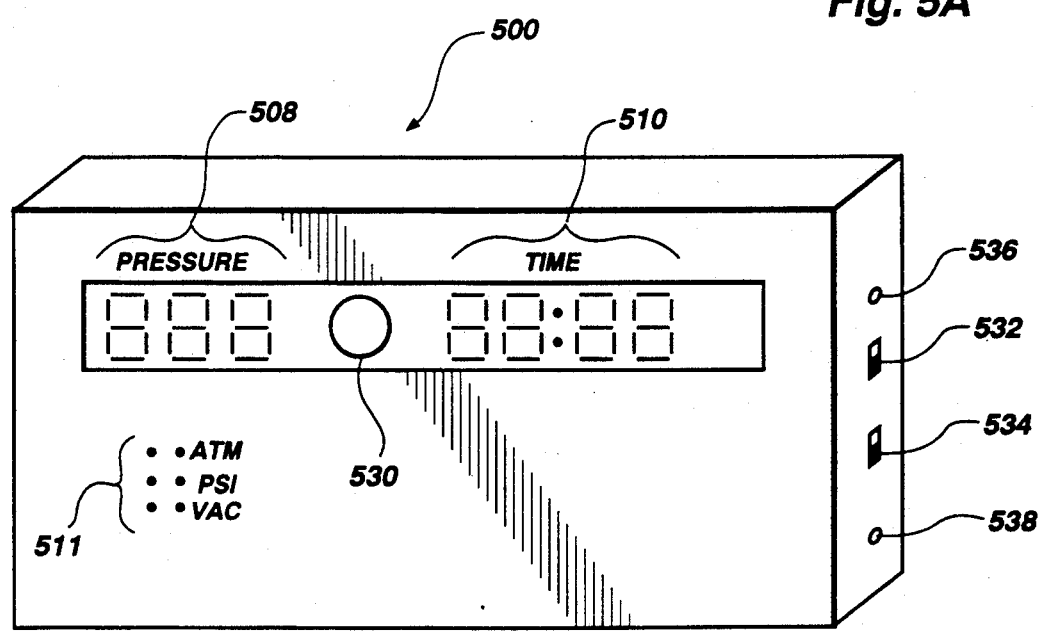
Fig. 5B

BALLOON CATHETER INFLATION SYRINGE WITH REMOTE DISPLAY

RELATED APPLICATIONS

This application is a continuation-in-part of application Ser. No. 07/707,671 filed May 30, 1991, now abandoned.

BACKGROUND OF THE INVENTION

FIELD

The invention relates to medical monitoring technology and more particularly to a monitor for a device used in angioplasty.

STATE OF THE ART

Balloon angioplasty, technically referred to as percutaneous transluminal angioplasty, is a procedure performed by a cardiologist on a patient under local anesthesia to open arteries blocked with plaque or other fatty deposits. A catheter with a dilatable (inflatable or deflatable) balloon at or near its tip is threaded into and through an artery and to the stenotic region. The balloon is then inflated thereby compressing the plaque against and into the arterial wall. In this manner the vessel's interior diameter is widened to again permit sufficient flow of blood. This procedure is utilized in the peripheral arteries as well as the coronary arteries. A balloon catheter is described and illustrated in U.S. Pat. No. 4,519,403.

Typically, the balloon is inflated utilizing a fluid such as a mixture of equal parts of a contrast media and saline solution, which fluid exerts the dilation pressure. An inflation syringe assembly or device is utilized to deliver the inflation medium or fluid to the balloon as well as to provide the pressure needed for dilation. Continuous pressure readings can be obtained by having the inflation syringe assembly coupled in series to a pressure reading device such as a manometer.

It is important that the inflation syringe assembly not only deliver fluid and maintain the pressure but also, in particular, release the pressure rapidly when needed. Various designs of syringe assemblies have been found capable of delivering fluid to a predetermined pressure, but none have proved entirely satisfactory. Some devices do not adequately maintain a predetermined pressure for a sufficient period of time as might be required by the physician. Instead, such devices tend to "leak" due to inadequate positive pressure control, which adds a further and troublesome complexity to the procedures. In order to obtain the requisite mechanical advantage in positively and incrementally inflating the balloon to higher pressures such as on the order of 450 psi and above, the typical structure provides threaded advancement, usually including a syringe piston that is advanced by a screw threaded rod engaged with a longitudinally fixed mating threaded member.

This type of positive threaded action may provide the requisite controlled incremental pressurization of the balloon, but retraction of the piston at the relatively slow rate achievable in a threaded device is not acceptable when emergency depressurization is needed. In the event of an emergency, the balloon should be deflated as quickly as possible. To achieve more rapid deflation, syringe devices having a threaded advancement have been constructed with threaded mating members which are manually movable to disengage from a threaded rod. This design permits somewhat more rapid retraction of the threaded rod and its attached syringe piston.

While complete disengagement in a time period of on the order of less than one half of a second is extremely important, known devices such as those described above take at least one second or longer at higher pressures. Furthermore, such previous devices lack sufficient leverage for rapid disengagement of the threadedly engageable member. Thus it is extremely difficult, and sometimes impossible, to obtain complete disengagement at pressures of from about 100 to about 150 psi and above.

Typical quick-release syringe devices heretofor disclosed in the art include those described in U.S. Pat. No. 4,832,692 to Box et al., and U.S. Pat. No. 4,723,939 to Goodin et al. The Box device utilizes an external lever located above the syringe barrel to release a splined block which engages/disengages a threaded plunger rod. The Goodin device employs a threaded plunger rod which is engaged/disengaged by a rotatable locking knob. Actuation of these release mechanisms may require a change of hand position on the syringe assembly.

Additionally, for safe and effective operation of the inflation syringe, it is important that the user have knowledge of the pressure exerted by the inflation syringe and the time elapsed with the balloon in the inflated state. Thus, the pressure sensor is associated with a monitoring readout device which displays the pressure readings. Previous such readout devices have generally taken the form of a box-like device attached to the pressure sensor by a data communication cable, the box to be placed for the user's viewing. If the cable is short, the box adds clutter to the operating area adjacent the patient. Alternatively, if the cable is long so that the device may be placed away from the immediate operating area, the cable between the readout device and the syringe is cumbersome and may obstruct movement of medical personnel in the area proximal to the patient.

Additionally, many such monitors do not include a timer for keeping track of time elapsed during balloon inflation. The user must refer to a separate timekeeping device such as a watch, stopwatch or clock to keep track of elapsed time. Looking back and forth between the timekeeping device and the pressure display is inconvenient and may slow the user's reaction time in operating the syringe.

Accordingly, a need remains for a quick release balloon pressurizing syringe, which provides depressurization within about ½ second. A need further remains for such a syringe which can be readily depressurized from pressures above 100 psi, preferably using only one hand to activate the disengagement of the piston.

A need further remains for a readout device for an angioplastic balloon catheter which can be remotely placed for viewing and provides a wireless transmission of data signals. A need further remains for such a monitor which includes a timekeeping display in a field of view adjacent to the pressure display.

SUMMARY OF THE INVENTION

A syringe assembly for inflating/deflating a balloon catheter has been invented which includes a trigger-actuated, quick-release mechanism for immediately deflating an inflated balloon. The trigger mechanism cooperates with the pistol-grip handle which is part of the syringe rear of the syringe assembly and is generally raked transversely to the longitudinal axis of the barrel of the syringe assembly. The trigger is preferably located forward of the handle and is positioned so that anyone gripping the handle may, with the same hand, easily grip, i.e., squeeze, the trigger to actuate the quick-release mechanism.

The quick-release mechanism consists of a threaded block, typically with a threaded rod passing through an opening in the block. The crown of the opening typically has transverse splines (partial threads) which engage the threads of the threaded rod. A plunger is attached at the distal end of the threaded rod. The plunger fits tightly within the barrel of the syringe. As the threaded rod is turned, preferably clockwise, the plunger advances forward in the barrel, forcing fluid within the barrel through a catheter to a balloon to inflate the balloon.

The trigger mechanism, when actuated, forces the block in a direction such that the threads of the block are disengaged from the threads of the threaded rod, thereby permitting the threaded rod to be forced rearward by fluid pressure acting on the plunger to relieve pressure on the fluid in the barrel and in the balloon.

In a further embodiment, the inflation syringe is provided with apparatus for remotely displaying the inflation pressure within the syringe. The apparatus comprises a pressure transducer positioned to sense pressure within the syringe, a transmission unit connected to receive a pressure signal from the transducer and operable to wirelessly transmit a pressure message reflective of the pressure signal, and a monitor positionable at a distance from the transmission unit. The monitor includes reception means for receiving the pressure message, and a display for displaying a pressure value communicated in the pressure message.

In the illustrated embodiments, the transmission unit includes an infrared light (I/R) transmitter and the pressure message is transmitted in the form of I/R pulses. The transmission unit further includes a controller connected to the I/R transmitter, and operable to control the transmission of pressure messages. A timer key is also associated with the transmission unit for operation by a user to send clock messages to stop or start a timer which is located in the remote display unit.

The pressure signal produced by the transducer is an analog signal. Therefore, the transmission unit further includes an A/D converter for converting the analog signal to a digital signal prior to transmitting the digital signal as a pressure or clock message.

The remote display unit further includes at least one microcontroller for decoding the received pressure and clock messages. The display unit microcontroller is constructed to verify the accuracy of each biphase data bit within a message and to require reception of two matching messages within a specified time frame before updating the display. The remote display unit also includes a timer and an elapsed time display. The timer is operable by means of start clock and stop clock signals initiated by pressing the timer key on the inflator unit, to time an interval.

BRIEF DESCRIPTION OF THE DRAWINGS

FIG. 1 is an elevational, cross-sectional view of a balloon catheter inflation/deflation syringe having a trigger-actuated, pressure-release mechanism;

FIG. 2 is an elevational view of a threaded block which is configured and adapted to engage the threads of a threaded rod passing through the opening in the threaded block;

FIGS. 5 and 5A are respectively an external perspective view and a frontal view of an alternate embodiment of the inflation syringe;

FIG. 5B is a perspective view of a remote display used in the alternate embodiment;

DETAILED DESCRIPTION OF THE ILLUSTRATED EMBODIMENTS

Figure 3:
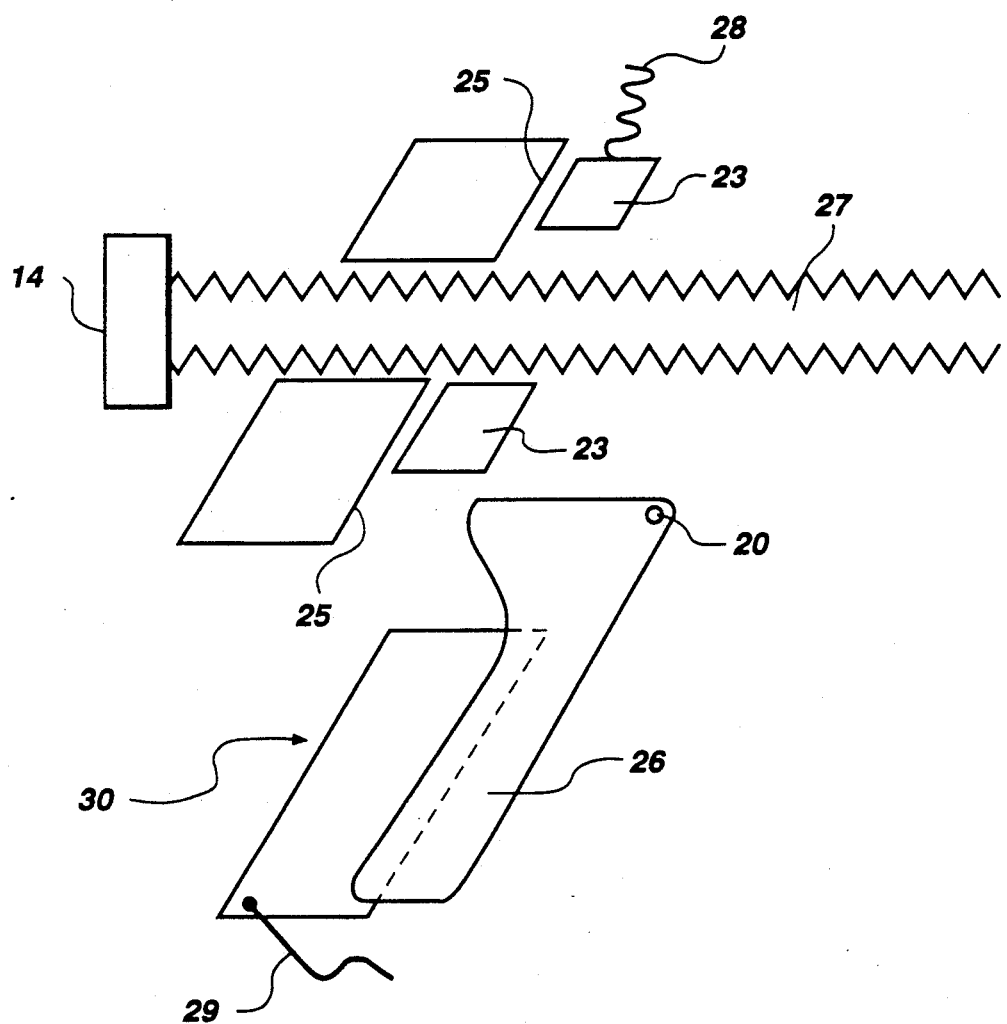
FIG. 3 is an elevational, cross-sectional view of a trigger-actuated pressure-release mechanism which has a fail-safe feature.

The instant invention involves a high-pressure syringe which employs a trigger-actuated, quick-release mechanism which engages/disengages a splined threaded block with a threaded plunger rod. The threaded plunger rod is rotated to advance the plunger to apply pressure to the fluid within the syringe barrel, which is directed to a balloon catheter to inflate the balloon. The trigger mechanism is positioned proximate a pistol-type handle (grip) which is approximately perpendicular or at a slight rake to the main barrel (and threaded rod) of the syringe.

The pistol grip and trigger mechanism provides an especially effective means for holding the syringe firmly while the threaded rod is rotated, yet provides a very quick access (movement of fingers) to actuate the trigger to release the threaded plunger and, consequently, to release pressure on the balloon catheter.

Further description of the invention may be facilitated by reference to the attached drawings, wherein FIG. 1, is a sectional, elevational view of a syringe with a pistol grip and a trigger release mechanism.

The syringe 10 illustrated in FIG. 1 has a barrel 11 which contains a plunger 12 connected to the forward (distal) end of a threaded rod 13 which extends from the rear of the syringe assembly. A knob 14 is attached to the proximal end of the threaded rod to provide a ready handgrip by which the rod can be rotated.

Rod 13 engages a threaded block 15 which has an internal opening larger than the threaded rod which opening contains threads only on its upper surface. The lower surface of the block opening is smooth. A spring member 16 biases the block 15 towards rod 13 so that the threads of the block engage the threads of the rod.

A handle (pistol grip) 17 projects at a slight rearward angle to the perpendicular from the syringe assembly housing 18. A trigger 19 is pivoted about pin 20 and cooperates with the handle 17 so that anyone operating the syringe can readily grip the handle 17 and squeeze trigger 19 to cause the top distal surface of the trigger, i.e. that top surface most remote from pin 20, to contact the bottom of block 15 to force block 15 upwards, thereby disengaging the threads of the block from the threads of the threaded rod 13. Any significant fluid pressure existing in barrel 11 will immediately force plunger 12 rearward, thereby immediately relieving pressure within the barrel.

The threaded block is illustrated in FIG. 2. The block 21 is a generally rectangular shape with a large opening 22 which has a curved crown 23 which is threaded with threads which run across the crown. The crown threads are generally transverse to the longitudinal axis of the barrel of the syringe. The crown 23 has a radius of curvature which is slightly greater than the radius of threaded rod 13. It is generally preferred that at least about 40% of the circumference of the threaded rod 13 be in contact with the crown 23 of the threaded block; however, the maximum contact should be less than about 40%. Obviously, the contact cannot exceed 50% or else the block won't release. Even at 50%, the risk of the block "hanging-up" and not releasing is too significant for good design if high tolerances are maintained between the "fit" of the threaded block to the threaded rod. If tolerances are large, then the circumferences of the threads in the threaded block may be approximately 50%.

The block opening 22 through which the threaded rod passes must be sufficiently high that enough room (area) is provided under rod 13 to permit block 21 to move upward a sufficient distance 50 that the threads of the block are completely disengaged from the threads of the rod. At a very minimum, the vertical distance of opening 22 below rod 13 must be at least the depth of the threads on rod 13 and preferably much more. Preferably, the "throw" (distance travelled) of the threaded block is at least twice the depth of the threads on the thread rod.

Another embodiment of the instant invention is illustrated in FIG. 3 wherein thread engagement between the threaded block and rod 13 requires constant pressure (force) on the trigger. This has many desirable features. During the inflation procedure the operator of the syringe must keep the handle squeezed to maintain engagement between the threaded rod and the threaded block. If an emergency occurs which requires deflation of the balloon catheter, the operator merely releases the trigger, which results in an immediate loss of pressure in the syringe and immediate deflation of the balloon.

The mechanism of FIG. 3 involves a threaded block 23 inclined at an angle from an axis perpendicular to the central longitudinal axes of the syringe. The threaded block is held in position against an inclined surface 25 which is a fixed surface which acts as a thrust bearing surface for the threaded block. While surface 25 could be perpendicular, the inclined surface takes advantage of the rearward pressure exerted on the plunger during inflation so that upon release of trigger 26, which must be kept in a squeezed or depressed condition to maintain engagement between the threaded rod 27 cause immediate disengagement between the threaded block and the threaded rod.

The device in FIG. 3 has a fail-safe aspect. It does not require an operator to perform some positive act, such as changing a hand position and squeezing a trigger, or a complete change of hand position as is required in the Goodin et al. or Box et al. devices.

Once inflation is accomplished, the trigger 26 of the FIG. 3 device has a locking mechanism which is a hinged clip 29, hingedly attached to the bottom of the handle 30. The hinged clip 29 engages the bottom of the trigger to hold the trigger in a depressed condition. The locking mechanism (clip) 29 can be readily unlocked by squeezing the handle 30 and trigger 26 and moving the distal end of the clip downward by a downward motion of the little finger. Thus, even with the trigger in a locked position, the pressure in the syringe may be rapidly released without any change in hand position.

Figure 4:
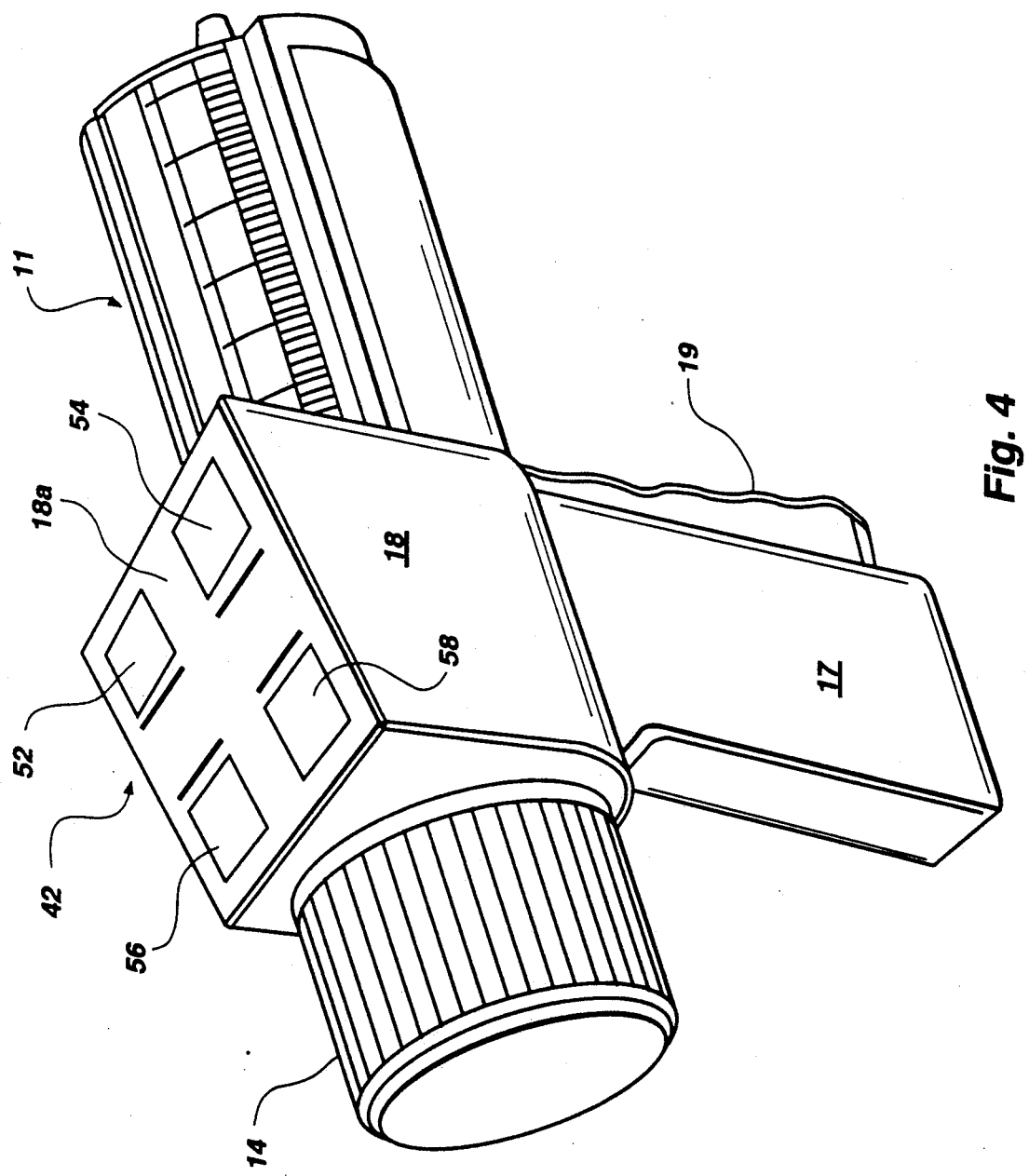
FIG. 4 is an external perspective view of a balloon catheter inflation syringe of the instant invention.

An external perspective view of the syringe assembly of the instant invention is presented in FIG. 4. The syringe body 18 of the syringe has a barrel 11 attached at its forward end. A knurled or ribbed knob 14 projects from the rear of the syringe body. Knurled knob 14 is connected to a threaded rod (not shown) at the rod's proximal end. The distal end of the rod is attached to a plunger.

Desirably, a pressure transducer 40 is disposed for reading the pressure within the syringe barrel (FIG. 1). Typically, transducer 40 produces an analog voltage output proportional to the applied pressure, which constitutes a pressure signal. Pressure transducer 40 is associated with an amplifier (not shown) for amplifying the pressure signal. The amplified pressure signal is then sent to a display unit indicated generally at 42 in FIG. 4.

In the embodiment of FIG. 4, display unit 42 includes panels 52, 54, 56, and 58 located on the top surface 18a of the syringe body 18. These display panels display operating information, such as the fluid pressure within the barrel sensed by transducer 40, elapsed time from a particular event, and the like.

As is apparent from the syringe assembly illustrated in FIG. 4, the instant invention provides a number of operational advantages over previous syringe assemblies. First, the operator of the syringe has a convenient, positive means, via the pistol-grip handle, of gripping (holding) the syringe assembly. The pistol-grip handle is shown in an opposite (polar) position to the display panels. However, the pistol-grip handle could be located from either side of the body 18, i.e., at 90° to the display panel. The bottom (polar) location, as shown in FIG. 4, is generally preferred since it can readily be operated effectively by either right- or left-handed operators.

The inflation syringe of the instant invention is particularly advantageous in being able to accommodate large volumes of inflation media, i.e., the device may have a barrel with large dimensions, either length or diameter or both. The barrel may have a greater diameter than typical syringes. For example, the displacement volume of the syringe plunger may be 30 cc or more. Thus, at a given pressure, e.g., 400 psi, there is more force on the large diameter plungers of the syringe of the instant invention than with conventional syringes. For example, the force on the plunger may be twice as great as for smaller plungers. This, of course, means that the disengagement force on the engagement/disengagement means must be significantly greater. The disengagement systems of the instant invention is particularly well suited for disengaging a threaded rod attached to a plunger which has a large force on it.

The pistol-type handle and trigger actuated release (disengagement) mechanism of the instant invention is particularly well suited for inflation syringes having a large displacement volume. The release mechanism can be actuated quickly and apply the larger amount of force which may be required to cause the disengagement means to disengage from the threaded rod. The juxtaposition of the pistol grip and trigger facilitates the application of large mounts of pressure on the trigger by squeezing of the hand.

In an alternate embodiment, the display 42 with panels 52, 54, 56, 58 on the syringe body is deleted and replaced by a remote display unit 500 (FIG. 5). Remote unit 500 can be positioned on a wall or the like for viewing by the user or other medical personnel. The handheld syringe unit 504 has a pressure transducer 506 positioned to sense pressure within the syringe near the end proximate the catheter attachment, and operably associated wireless transmission means 502. Wireless transmission means 502 is connected to receive and wirelessly transmit messages including pressure messages from transducer 506 to remote unit 500 which is positioned for convenient viewing by medical personnel. Remote unit 500 includes a pressure display 508 for displaying a pressure value reflective of the pressure sensed by transducer 506, and a time display 510 which indicates time elapsed from a user-designated start point.

Transmission means 502 includes I/R pulse means for sending digitally-coded I/R pulse sequences. The I/R pulse sequences include clock messages reflective of the start or finish of a time interval, or pressure messages communicative of the pressure sensed by transducer 506. In the illustrated embodiment, the I/R pulse means comprises two I/R LEDs 512, 514 disposed on the front surface 502A of transmission unit 502 (FIG. 5A). LEDs 512, 514 simultaneously transmit identical I/R pulse sequences. Optionally and desirably, LEDs 512, 514 are covered by a lens (not shown) which does not interfere with transmission of I/R pulses but which protects against contamination of the electronic components with fluids.

Figure 8:
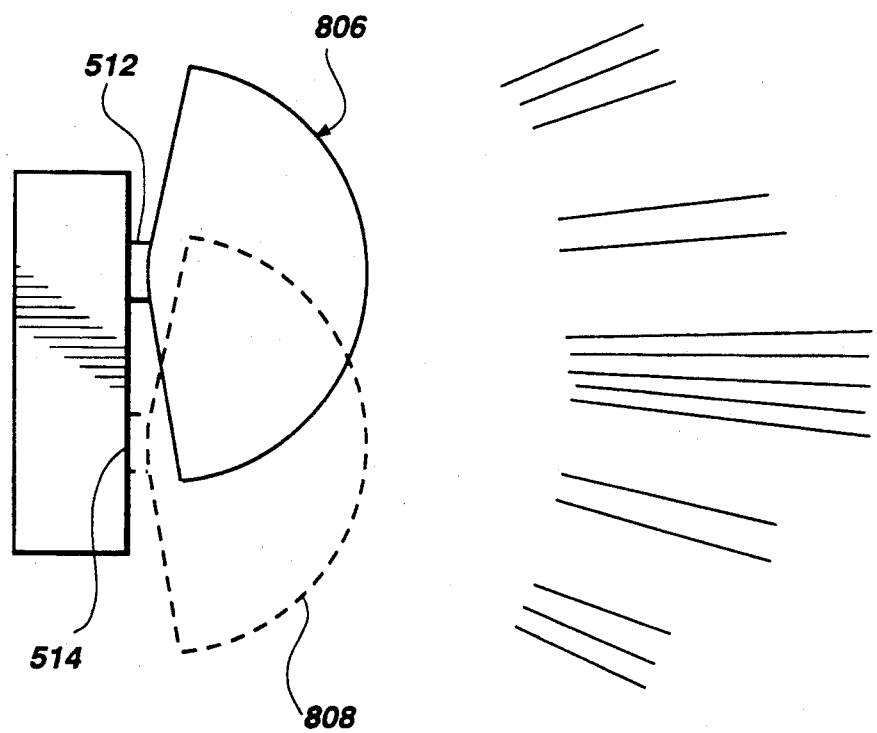
FIG. 8 is a diagram illustrating the overlap of transmission signals of a two-LED transmitter.

In the illustrated embodiment, LEDs 512, 514 each transmit an infrared signal subtending a transmission arc of about 165°. LEDs 512, 514 are arranged to have their respective transmission arcs 806, 808, overlapping (FIG. 8) preferably over an arc of about 100°. This arrangement provides a strong signal in the central overlap region with a minimum of parts, for more accurate and reproducible transmission. Alternatively, LEDs 512, 514 could be replaced by a single LED or by three or more LEDs. In another embodiment, one or more infrared laser diodes could replace the LED(s) as the infrared light transmitter.

Power key 516 is a momentary-type key for turning transmission means 502 on and off. Time key 518 is a momentary-type key for a user to press to designate the start or end of a time interval. In response to pressing of time key 516, transmission means 502 sends a clock message via I/R LEDs 512, 514. Transmission means 502 also has indicators 520, 522. Indicator 520 is turned on steady when the unit is on, and flashes when time key 518 is pressed to start a time interval. Indicator 522 is turned on when the handheld unit is initialized in an invalid condition, based upon the pressure sensed by transducer 506 when power key 516 is pressed to turn transmission means 502 on.

Remote display unit 500 includes a detector window for detecting the I/R pulse sequences, and a display 508 for displaying pressure values communicated in the transmitted digital signals. A set of indicators 511 indicates whether the pressure reading shown in pressure display 510 is in units of atmospheres, psi, or inches of mercury (the latter is only displayed if there is a below-atmospheric pressure in the syringe). Remote unit 500 also includes a time display 510 for displaying the time elapsed from a start point designated by a user pressing time key 516. Remote unit 500 further includes on/off switch 532 and units switch button 534 (both two-position switches); and jacks 536, 538. Jack 536 is a power jack for receiving an external power input, while jack 538 is for a chart recorder output.

In a further embodiment of the transmitter and remote display (not illustrated), the transmitting LEDs 512, 514 are positioned on the top surface 502B of the transmission means 502, instead of on the front surface 502A. The receiver portion of remote unit 500 is then positioned above the user, for example on the ceiling. The display portion is mounted for viewing on a wall or similar convenient viewing location, and is electrically connected by a cable to the receiver portion to receive the display signals.

The embodiment of the preceding paragraph offers some further advantages in that it is much easier for a user to keep the infrared transmitters aimed towards the remote receiver. The user has greater freedom of movement and the necessity for particular positioning of the patient and/or the user holding the transmitter syringe, so that the front 502A is aimed generally toward the remote receiver, is avoided. The associated cable of this embodiment is positioned on the ceiling and extends down from the upper edge of walls or the like, so it will not be an obstacle to personnel moving about the area.

Figure 6:
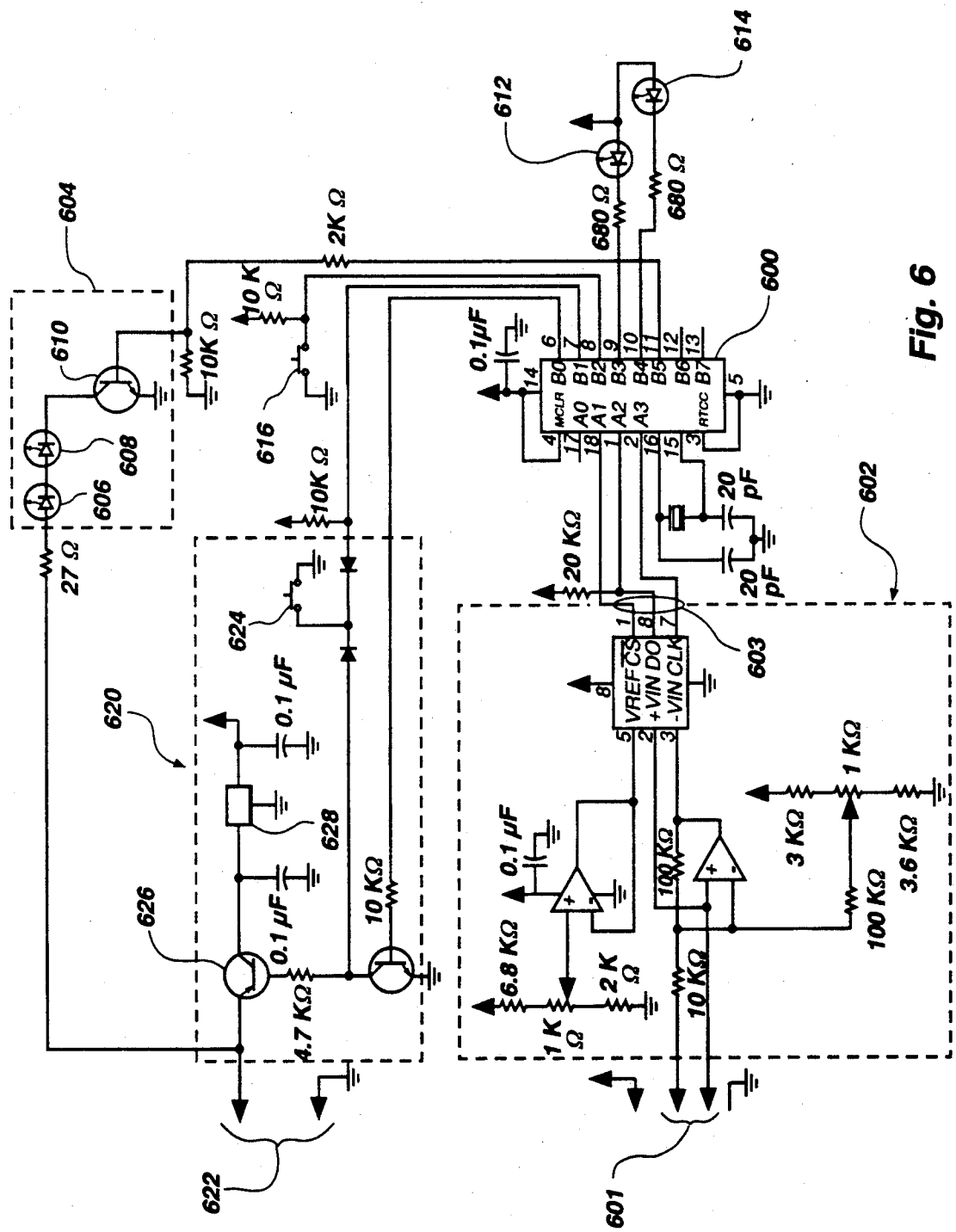
FIG. 6 is a circuit diagram of a transmission means of the readout apparatus.

FIG. 6 depicts circuitry for a working embodiment of transmission means which may be incorporated into syringe body 18. A microcontroller 600 comprises a central processing unit (CPU), read only memory (ROM) random access memory (RAM), timer unit and watchdog timer. Microcontroller 600 is here selected to be a microchip 16C54, obtained from Microchip Technology Corp. having a ROM of the OTP (one-time programmable) type. However, a chip with an EEPROM or EPROM could also be used. In the illustrated embodiment, the OTP ROM is programmed with the appropriate software prior to installation in the circuit board. Microcontroller 600 is constructed to perform or control all major functions associated with syringe 10, including all required timing functions, generation of the IR transmission, managing of the power control circuit, and the reading and averaging of pressure signals received from transducer 506.

Transducer 506 provides pressure signals, which are electrical signals proportional to sensed pressures, at inputs 601 which is connected to an analog-to-digital (A/D) converter 602 for converting the analog pressure signal to a digital signal communicative of the sensed pressure. This is because a digitally coded signal is preferred for wireless transmission, whereas a typical pressure transducer outputs an analog electrical signal. A/D converter 602 is in turn connected to microcontroller 600 at outputs 603.

In a preferred embodiment, microcontroller 600 takes readings at 100 millisecond intervals, or in other words, ten times a second. Further preferably, microcontroller 600 computes a computed pressure reading which is obtained by averaging two current readings, then taking the result and averaging it with the previously computed pressure reading. The new computed pressure reading thus obtained is sent to an infrared transmitter 604 for transmission as infrared light pulses to the receiving unit. Averaging the pressure readings in such a fashion smooths out noise.

Microcontroller 600 is further constructed to vary the rate of message transmission according to the stability of the pressure signal received from transducer 506. The pressure signal is sampled about every 100 milliseconds. If the pressure changes by 2 psi or less, messages are sent at one-second intervals. If the pressure changes by more than 2 psi, pressure messages are sent five times per second. By so varying the transmission rate, drain on the battery is reduced and the accuracy of transmission is increased. The maximum display update rate is thus 5 times a second. Such an update rate allows pressure changes to be rapidly reflected in the display, yet holds individual values long enough that they can be easily read by a viewer.

Infrared transmitter 604 comprises two infrared LEDs 606, 608 (equivalent to 512, 514 in FIG. 5) in series with a transistor 610 which functions as a power switch. Transistor 610 is connected to microcontroller 600 to be controlled in an on/off fashion.

Indicators 520, 522 of FIG. 5 are here embodied as LEDs 612, 614, which are connected to be operated by micro controller 600 to indicate power on/timing and invalid set-up, respectively. LED 612 is responsive to switch 616 which is a momentary switch activated by pressing of time key 518. When time key 518 is pressed, an I/R clock message is sent by transmitter 604. If the previous clock message was a stop clock message, the instant message is a start clock message, and vice-versa. Upon initiation of a start clock message, the timing LED 612 is flashed. Otherwise, timing LED 612 is steadily on as long as the unit is turned on.

Power management functions are effected through power control circuitry indicated generally at 620. In the working embodiment, power is received at inputs 622 from a 9 volt battery which is installed in the hand-held syringe unit. An on/off switch 624 governs the supply of power to microcontroller 600. When switch 624 is turned "on", a transistor switch 626 is activated to send power to a voltage regulator 628. Voltage regulator 628 outputs +5 volts which powers microcontroller 600 and A/D converter 602. IR LEDs 606, 608 of transmitter 604 are connected to receive +9 volts directly from inputs 622.

Microcontroller 600 is further desirably constructed to perform an initialization routine. The initialization routine begins when power is first supplied to the transmission means. Lighting of power LED 612, which is connected to microcontroller 600, indicates that power is on. Next, the current pressure sensed by transducer 506 is read, and if it is more than 10 psi below atmospheric pressure, or more than 25 psi above atmospheric, an invalid setup LED 614 is lit. The power is automatically cut off via transistor switch 626 two (2) seconds after the on/off switch 624 is released. If the pressure sensed is within the above-cited lower and upper limits, the current pressure reading is used as a zero offset value for the current session.

Figure 7:
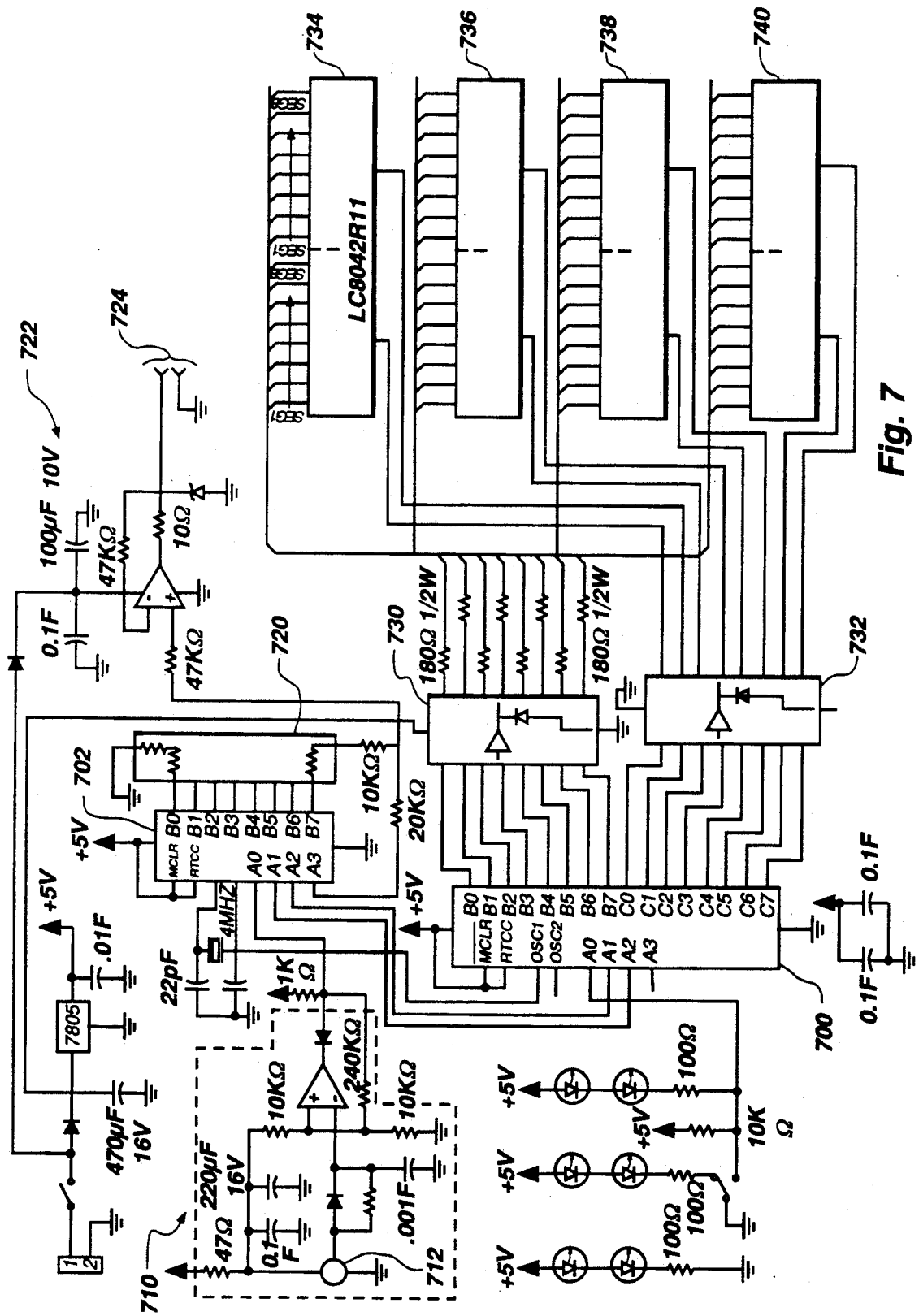
FIG. 7 is a circuit diagram of a remote receiver/display unit of the readout apparatus.

Turning to FIG. 7, circuitry for a working embodiment of the remote display unit 500 will be described. Remote unit 500 has two microcontrollers 700, 702. This is because of the time critical nature of the two tasks of the remote unit: reception of the wireless transmission and display multiplexing.

Microcontroller 702 handles the timing and data verification required for receiving the I/R transmission sent from transmitter 604 on syringe 10. Microcontroller 702 decodes the transmitted digital pressure signals and converts the value of pressure communicated by the transmitted signals from psi to atmospheres. In the working embodiment, microcontroller 702 is selected to be a 16C54, the same chip as used in the transmission unit. Microcontroller 702 is connected to receive filtered signals reflective of the transmitted pressure signals from I/R receiver generally indicated at 710. I/R receiver 710 comprises a hybrid I/R receiver 712 having built-in automatic gain control, with operably associated bypass filtering.

Optionally, in order to provide an electrical signal output reflective of the pressure signals for a chart recorder, an R2R resistor network chip 720 obtained from Bourns Co. is connected to microcontroller 702 to function as a digital-to-analog (D/A) converter. Chip 720 is in turn connected to scaling and protection circuits indicated generally at 722, which output the analog pressure signal at jacks 724. A chart recorder may be connected to receive the analog pressure signals at jacks 724.

Microcontroller 702 is constructed to decode the received pressure and clock messages as follows. In the working embodiment, both pressure and clock messages are transmitted in the form of biphase data bits each having first and second portions. Transmitter controller 600 generates the biphase bits such that if the first portion is high, the second portion is low, and vice-versa. During the time required for transmission of one portion of the biphase bit (about 500 microseconds), the received signal is sampled many times. Microcontroller 702 then determines, based on a majority of the samples, as to whether the immediately received portion of the biphase bit is high or low. If a bit is received in which both the first and second portions are high, or both are low, the message is discarded. This system of requiring that each biphase bit include both a high and a low portion, helps to eliminate erroneous messages caused by noise and stray infrared signals picked up by the detector 530.

Microcontroller 702 is further constructed to wait for two transmitted messages to match exactly before considering the message valid and sending a message signal to display controller 700. Transmission means 502 is constructed to send three copies of each message per pressure reading, so that one may be lost without loss of the message. Each pressure message comprises nine biphase bits, while each clock message comprises six biphase bits. The difference in length of the two types of messages allows microcontroller 702 to distinguish between them.

In the illustrated embodiment, pressure messages are communicative of the pressure reading in PSI. If a user desires, the pressure value may be displayed in atmospheres by operation of the Units switch 534 on the display unit. If atmospheres are selected, microcontroller 702 makes a conversion from PSI to atmospheres. Should the pressure go negative, a conversion from PSI to inches of mercury (inHg) is done by display microcontroller 702. Negative pressure is always displayed as inHg.

Microcontroller 700 is constructed to operate the seven segment display. In the working embodiment, microcontroller 700 is selected to be a MICROCHIP 16C55, obtained from Microchip Technology Corp. which is functionally identical to the 16C54 except that it has more input/output pins. A high-side driver 730 (chip UDN2981) and a low-side driver 732 (chip ULN2804) obtained from Microchip Technology Corp. are connected to receive multiplexing LED control signals from microcontroller 700. Drivers 730, 732 are in turn connected to drive LED segments 734, 736, 738, 740 which each comprise two seven segment LED displays. Drivers 730, 732 are required because microcontroller 700 does not have sufficient drive capability to drive LED segments 734, 736, 738, 740.

Microcontroller 700 controls the output of drivers 730, 732 to provide binary-to-seven segment conversion of the data and display multiplexing of LED segments 734, 736, 738, 740. The seven-segment LED displays are multiplexed at a ⅛ duty 125 Hz rate. Multiplexing is used to provide a low parts count hardware design. LED segments 734, 736, 738, 740 are identical and are here selected to be LC8042R-11 chips.

Microcontroller 700 is further operable to perform time-keeping functions. A clock message received by microcontroller 702 (the receiver microcontroller) is sent directly to microcontroller 700 (the display microcontroller). When a clock message signalling the start of a time interval is received, the display controller increments the time display by one second every second to a maximum value of 99 minutes 59 seconds. When a clock stop or clock reset message is received, the time display is not incremented. If a clock reset message is received, the clock counters are reset to zero. If no messages are received during any 3 second interval, microcontroller 700 flashes all seven (7) segment displays at a 1 Hz rate to inform the user of an interruption in I/R communications.

Microcontrollers 700, 702 are mutually interconnected and adapted to provide for the exchange of information between them. Accordingly, both microcontrollers 700, 702 are constructed to perform an efficient, two wire, bi-directional, serial communication routine.

The wireless transmission unit provides several advantages for medical personnel. The display can be positioned so that the user of the syringe unit can quickly look from the remote unit to other displays such as EKG, etc, which are nearby. No wires are needed to communicate the data to the display, so no extra wires are added to become obstacles to other medical personnel moving in the area. The provision of a timer easily operated on the handheld unit, with an elapsed time display adjacent the pressure display on the remote unit, is a great convenience for a user. Many users formerly used a watch or room clock to time inflation/deflation procedures, or had a technician keep time and call it out, the latter method further adding to confusion and noise in the operating area.

A wireless transmitter in conjunction with a remote receiver/display unit may provide advantages for other types of surgical/medical instruments and procedures besides angioplasty. The system could be adapted to any handheld device which can include a sensor positioned to sense a critical operating condition of the device or an organic condition of the patient's tissues near the device, or when precise timing of procedures with the handheld unit is needed. Such a sensor should be adapted to produce an electrical signal reflective fo the condition being sensed.

The wireless transmitter in association with a pressure transducer, combined with the remote monitor, could also be adapted to any inflation device structured for pressurizing an inflatable vessel, not necessarily for a medical device.

Various advantages are provided by the IR transmitter/remote receiver system. The I/R signal is simple and accurate for relatively short-range line-of-sight transmission, and will not interfere with other electrical signals in nearby medical monitors and equipment. The handheld unit (e.g. the unit of FIG. 5) is completely self-contained including power source, and thus does not entail wires or cables which obstruct movement of the user or of medical personnel in the crowded surgical area. Also, the I/R transmitter consumes a relatively small amount of power.

While specific embodiments of the invention have been illustrated and described herein, the invention is not intended to be limited thereto, but is to include all the embodiments, variations and modifications encompassed within the appended claims.

What is claimed is:

1. A medical device and transmitter apparatus for sensing and transmitting a sensed parameter to a remote display unit, comprising:
   a medical device having a sensor for sensing a condition selected from the group consisting of an operating condition of said medical device and a condition of a patent to whom said medical device is being applied and for providing a sensor signal reflective of said condition;
   a transmitter unit communicating with said sensor to receive said sensor signal and to transmit a sensor message indicative of said condition;
   a power source connected to said transmitter remit to power said transmitter unit; and
   a remote display device placeable at a distance from said transmitter unit, connectable to a second power source to receive operating power, and including:
      signal reception means for receiving said wireless transmitted sensor message and providing a sensor display signal in response thereto, and
      sensor display means connected to said signal reception means for receiving said sensor display signal and providing a display reflective thereof,
   wherein said wireless transmitter is an infrared light transmitter, said sensor message comprises an infrared signal, and said remote display device includes infrared detection means for receiving said infrared signal sensor message and signal translation means connected to said infrared detection means for receiving and translating said infrared signal into a display signal indicative of thereof.

2. The apparatus of claim 1, wherein said infrared light transmitter comprises at least one infrared LED having a transmission arc constituting an angle based at said infrared LED through which said infrared LED effectively transmits said infrared signal.

3. The apparatus of claim 2, wherein said infrared light transmitter comprises a plurality of LEDs mutually positioned to have their respective said transmission arcs overlapping.

4. The apparatus of claim 2, wherein said infrared light transmitter comprises a pair of LEDs positioned to have said respective transmission arcs overlap by about 100°.

5. The apparatus of claim 1, wherein said infrared light transmitter comprises at least one infrared laser transmitter.

6. The apparatus of claim 1, wherein said sensor signal is an analog signal, and said transmission means further includes an A/D (analog to digital) converter for converting said analog signal to a transmittable digital signal constituting said sensor message.

7. The apparatus of claim 6, wherein said transmitter unit further includes a controller connected to said A/D converter to receive said digital signal and operable to control the transmission of said sensor message.

8. The apparatus of claim 7, wherein said transmitter unit further includes a timer key connected to said controller, said controller being further operable to control said wireless transmitter to transmit a clock message in response to pressing of said timer key by a user.

9. The apparatus of claim 8, wherein said remote display unit further includes
a time display, and
a display controller connected to said time display and said receiving unit, said display controller being operable to count time elapsed from receipt of a start clock message and to provide time display signals reflective thereof to said time display.

10. The apparatus of claim 7, wherein said controller is operable to compute said sensor message by averaging at least two successively received sensor signals to produce an averaged sensor signal.

11. The apparatus of claim 10, wherein said controller is further operable to compute said sensor message by averaging said averaged sensor signal with an immediately preceding averaged sensor signal, to produce a twice-averaged sensor signal.

12. Apparatus which includes a remote display and an inflator for inflating a balloon catheter, comprising:
operable associated therewith to sense pressure within said inflator, and to provide a pressure signal reflective thereof;
a transmission unit connected to receive said pressure signal from said pressure transducer, and operable to wirelessly transmit a pressure message in response thereto, said transmitter unit including a wireless transmitter;
a power source connected to power said transmitter unit; and
a display device constructed to be positionable at a distance from said transmitter unit, connectable to a second power source to receive operating power, and operable to receive said pressure message and to provide a pressure display reflective thereof,
wherein said wireless transmitter is an infrared light transmitter, said pressure message comprises an infrared light signal, and said display device further includes infrared reception means for receiving said infrared light signal, and signal translation means for translating said infrared light signal into a pressure display signal indicative of said pressure message.

13. The apparatus of claim 12, wherein said transmission unit further includes a controller connected to said wireless transmitter and to receive said pressure signal, said controller being operable to control the transmission of said pressure message by said wireless transmitter.

14. The apparatus of claim 13, wherein said transmission unit further includes a timer key connected to said controller, said controller being further operable to control said wireless transmitter to transmit a clock message in response to pressing of said timer key by a user.

15. The apparatus of claim 14, wherein said pressure signal is an analog signal, and said transmission unit further includes an A/D converter connected to said pressure transducer for converting said analog signal to a digital signal, and connected to said controller to send said digital signal thereto; and wherein said infrared light transmitter transmits said pressure message and said clock message in a digital format.

16. The apparatus of claim 15, wherein said display unit further includes
a time display, and
a display controller connected to said time display and said receiving unit, said display controller being operable to count time elapsed from receipt of a start clock message and to provide time display signals reflective thereof to said time display.

17. The apparatus of claim 12, wherein said infrared light transmitter comprises at least one infrared LED having a transmission arc constituting an angle based at said infrared LED through which said infrared LED effectively transmits said infrared light signal.

18. The apparatus of claim 17, wherein said infrared light transmitter comprises a plurality of LEDs simultaneously transmitting said infrared light signal, and arranged to have their respective transmission arcs overlapping.

19. An apparatus for performing transluminal angioplasty with a balloon catheter and for displaying information relative thereto, comprising an inflator to inflate a balloon catheter;
a pressure sensor positioned within said inflator for sensing the pressure exerted within said inflator to inflate said balloon catheter, said pressure sensor producing a pressure signal indicative of said pressure;
a signal communicating unit associated with said inflator, connected to receive said pressure signal, and including a wireless transmitter operable to wirelessly communicate a pressure message reflective of said pressure signal;
a remote monitor positionable at a distance from said signal communication unit, and operable to receive said pressure message, translate said pressure message into a pressure display signal, and display a pressure value indicative of said pressure display signal; and
wherein said pressure signal is an analog signal, said wireless transmitter is constructed to transmit said pressure message in a digital format, and said signal communication unit further includes an A/D converter connected to convert said analog signal to a digitally-formatted signal and provide said digitally-formatted signal to said wireless transmitter.

20. The apparatus of claim 19, wherein said wireless transmitter is an infrared light transmitter.

21. The apparatus of claim 19, wherein said signal communication means further includes a controller key connected to said controller, said controller being operable to control said wireless transmitter to transmit a clock message in response to operation of said timer key by a user.

22. The apparatus of claim 21, wherein said remote monitor further includes
a display controller connected to said receiving unit, and operable to count time elapsed from receipt of a start clock message and to provide time display signals reflective thereof; and
a time display connected to receive said time display signals and to display the elapsed time indicated thereby.

23. The apparatus of claim 20, wherein said infrared light transmitter comprises at least one infrared LED.

24. An inflation syringe for inflating an attached inflatable member, comprising:
a pressurizing chamber for pressurizing a balloon catheter;
a pressure sensing transducer in communication with said pressurizing chamber, said transducer producing an analog electrical signal having a magnitude proportional to the pressure being sensed;
conversion means electrically connected with said pressure sensing transducer for converting said analog electrical signal to a digital signal reflective of the magnitude of said analog signal;

IR transmitter means electrically connected with said conversion means for transmitting said digital signal in the form of an IR signal in a format; and a power supply electrically connected to power said conversion means and said transmitter means.

25. The inflation syringe of claim 24, further including a transmission controller communicatively connected with said conversion means and said transmitter means for receiving said digital signal and controlling said transmitter to transmit said digital signal in accordance with a desired protocol.

26. The inflation syringe of claim 25, further including a timer key mechanically adapted to said inflation syringe, electrically connected to said transmission controller and said transmitter means, and operable by a user to initiate the transmission of a clock message indicative of a user-selected start or end of a timed interval.

27. The inflation syringe of claim 25, wherein said controller is operable to compute an averaged digital signal by averaging at least two successively received digital signals, and to cause said transmitter means to transmit said IR in a form reflective of said averaged digital signal.

* * * * *

UNITED STATES PATENT AND TRADEMARK OFFICE
CERTIFICATE OF CORRECTION

PATENT NO. : 5,215,523

DATED : 6/1/93

INVENTOR(S) : Williams et al.

Page 1 of 2

It is certified that error appears in the above-indentified patent and that said Letters Patent is hereby corrected as shown below:

In Column 2, line 13, change "heretofor" to --heretofore--;

In Column 2, line 67, after "syringe" (1st occurrence) insert --assembly. The pistol-grip handle is positioned near the--;

In Column 5, line 42, change "axes" to --axis--;

In Column 5, line 50, after "threaded" insert --block and the threaded rod 27, both the force of the disengagement spring 28 and the rearward force on the threaded--;

In Column 5, line 31, after "block" insert --23--;

In Column 5, line 31, change "13" to --27--;

In Column 5, line 43, after "block" insert --23--;

In Column 6, line 61, change "mounts" to --amounts--;

In Column 7, line 11, change "start" to --starting--;

In Column 7, line 52, after "window" insert --530--;

In Column 7, line 57, change "510" to --508--;

In Column 8, line 24, after "(ROM)" insert a comma;

In Column 8, line 54, insert a hyphen between "previously" and "computed";

In Column 9, line 12, delete the space between "micro" and "controller";

In Column 9, line 56, change "transmission" to --transmissions--;

In Column 9, line 68, change "bypass" to --bandpass--;

UNITED STATES PATENT AND TRADEMARK OFFICE
CERTIFICATE OF CORRECTION

PATENT NO. : 5,215,523

DATED : 6/1/93

INVENTOR(S) : Williams et al.

It is certified that error appears in the above-indentified patent and that said Letters Patent is hereby corrected as shown below:

In Column 11, line 30, change "etc." to --etc.,--

In Column 12, line 19, change "remit" to --unit--;

In Column 12, line 38, delete "of";
In Column 13, line 20, before "operable" insert --a balloon catheter device containing a pressure transducer--;

In Column 13, line 20, change "operable" to --operably--;

In Column 14, line 22, change "communicating" to --communication--;

In Column 14, line 43, after "controller" insert --connected to control said wireless transmitter, and a timer--;

In Column 16, line 12, after "IR" insert --signal--;

Signed and Sealed this

Nineteenth Day of April, 1994

Attest:

BRUCE LEHMAN

Attesting Officer

Commissioner of Patents and Trademarks